United States Patent

Greindl et al.

[11] Patent Number: 5,817,864
[45] Date of Patent: Oct. 6, 1998

[54] PROCESS FOR THE PREPARATION OF GLYCINE-N, N-DIACETIC ACID DERIVATIVES

[75] Inventors: Thomas Greindl, Neuburg; Alfred Oftring, Bad Dürkheim; Gerold Braun, Ludwigshafen; Jochen Wild, Ruppertsberg; Birgit Potthoff-Karl; Georg Schuh, both of Ludwigshafen, all of Germany

[73] Assignee: BASF Aktiengesellschaft, Ludwigshafen, Germany

[21] Appl. No.: 653,023

[22] Filed: May 24, 1996

[30] Foreign Application Priority Data

May 29, 1995 [DE] Germany .................. 195 18 987.6

[51] Int. Cl.$^6$ .................................. C07C 229/02
[52] U.S. Cl. ........................... 560/171; 562/571
[58] Field of Search .............................. 560/171; 562/571

[56] References Cited

U.S. PATENT DOCUMENTS 2,500,019  3/1950  Bersworth ........................ 260/534
3,733,355  5/1973  Harris et al. ...................... 260/534

FOREIGN PATENT DOCUMENTS 2 027 972    4/1971   Germany .
WO 94/29421  12/1994  WIPO .

*Primary Examiner*—Allen J. Robinson
*Assistant Examiner*—Barbara Badio
*Attorney, Agent, or Firm*—Oblon, Spivak, McClelland, Maier & Neustadt, P.C.

[57] ABSTRACT

Glycine-N, N-diacetic acid derivatives are prepared by reacting corresponding 2-substituted glycines, 2-substituted glycinonitriles, doubled glycines, or precursors of the glycine derivatives with formaldehyde and alkali metal cyanide. The reaction is conducted in an aqueous medium at a pH of 8 to 14. From 0, 5 to 30% of the amount of alkali metal cyanide required for the reaction are added to the glycine derivatives or precursors thereof Subsequently, the remaining amount of alkali metal cyanide and the formaldehyde are simultaneously metered in over a period of from 0.5 to 12 hours.

6 Claims, No Drawings

PROCESS FOR THE PREPARATION OF GLYCINE-N, N-DIACETIC ACID DERIVATIVES

Preparation of glycine-N,N-diacetic acid derivatives by reacting glycine derivatives or their precursors with formaldehyde and alkali metal cyanide in aqueous alkaline medium.

The present invention relates to a process for preparing glycine-N,N-diacetic acid derivatives by reacting glycine derivatives or their precursors with formaldehyde and alkali metal cyanide in aqueous alkaline medium.

The standard products currently used in the typical applications of complexing agents and builders, such as highly alkaline cleaners and domestic detergents, are aminopolyphosphonates, polycarboxylates or ethylenediaminetetraacetic acid (EDTA). These products undergo biodegradation only with difficulty, which is why there is a need for effective and, at the same time, low-cost substitutes which are readily biodegradable.

One alternative to the above substances is nitrilotriacetic acid (NTA) which is readily biodegradable but has distinct disadvantages in effect by comparison with EDTA and is often unwanted for toxicological reasons. Methylglycine-N,N-diacetic acid ($\alpha$-alanine-N,N-diacetic acid, MGDA) is a non-toxic, readily biodegradable complexing agent with a higher stability constant than NTA. The use of MGDA and related glycine-N,N-diacetic acid derivatives for the detergents and cleaner sector and for numerous novel applications, and novel synthetic routes to such substances are described in WO-A 94/29421 (1).

The synthesis of MGDA with the aid of chloroacetic acid has been known for a long time. This route is now no longer economic because of the unavoidable production of sodium chloride and the formation of organochlorine impurities, nor is it in accord with the times from the ecological standpoint. It is also necessary, in order to obtain high yields, to use excess chloroacetic acid, which is associated with the formation of glycolic acid, oxodiacetate and organochlorine compounds as byproducts. Other haloacetic acids result in a similar range of byproducts. The removal of the inorganic salts such as sodium chloride which are produced in stoichiometric amounts is elaborate and costly.

An economic and, at the same time, environmentally acceptable method for preparing aminopolycarboxylates is, in principle, the Strecker reaction of amino acids. The synthesis of MGDA by means of the Strecker reaction is described in (1).

DE-A 20 27 972 (2) describes the "acidic" variant of the Strecker reaction of unsubstituted glycine with formaldehyde and hydrocyanic acid. In this case, N,N-bis(cyanomethyl)glycine is formed from glycine and can be isolated in high purity. The disadvantage of the "acidic" variant is the use of free hydrocyanic acid and the need for an additional hydrolysis step after removal of the nitrile.

The "alkaline" variant of the Strecker reaction is described in general form, for example, in U.S. Pat. No. 3,733,355 (3). However, the examples detailed therein show that a high proportion of byproducts, especially unwanted glycolic acid, always occurs; this can be concluded from the maximum conversions of only about 89%.

U.S. Pat. No. 2,500,019 (4) mentions the reaction of $\alpha$-amino acids with formaldehyde and sodium cyanide in general and, taking the example of unsubstituted glycine from protein hydrolysate, prepares nitrilotriacetic acid. However, the glycine which is the amino acid used in this process is particularly reactive because it is unsubstituted. In addition, the NTA which forms is, because of its high symmetry, thermodynamically preferred to nonsymmetrical compounds and is particularly easily formed.

The reaction of more sterically hindered amino acids such as alanine in high yields with minimal proportions of NTA is particularly difficult. Glycine sodium salt is prepared from protein hydrolysate in (4). A protein hydrolysate usually contains other amino acids in the mixture so that the Strecker reaction does not give an NTA-pure product in this case.

It is an object of the present invention to provide a simple and economic synthetic route to glycine-N,N-diacetic acids such as MGDA with the intention of maximizing the overall yield with, at the same time, high purity of the products and aiming at low NTA contents, where possible below 2% by weight.

We have found that this object is achieved by a process for preparing glycine-N,N-diacetic acid derivatives of the general formula I

where

R is $C_1$-$C_{30}$-alkyl or $C_2$-$C_{30}$-alkenyl, each of which can additionally carry as substituents up to 5 hydroxyl groups, formyl groups, $C_1$-$C_4$-alkoxy groups, phenoxy groups or $C_1$-$C_4$-alkoxycarbonyl groups and can be interrupted by up to 5 nonadjacent oxygen atoms, or alkoxylate groups of the formula -$(CH_2)_k$-O-$(A^1O)m$-$(A^2O)_n$-Y, where $A^1$ and $A^2$ are, independently of one another, 1,2-alkylene groups having 2 to 4 carbon atoms, Y is hydrogen, $C_1$-$C_{12}$-alkyl, phenyl or $C_1$-$C_4$-alkoxycarbonyl, and k is 1, 2 or 3 and m and n are each from 0 to 50, it being necessary for the total of m+n to be at least 4 phenylalkyl groups having 1 to 20 carbon atoms in the alkyl, phenyl, a five- or six-membered unsaturated or saturated heterocyclic ring which has up to three hetero atoms from the group consisting of nitrogen, oxygen and sulfur and which can additionally be benzo-fused, it also being possible for all the phenyl nuclei and heterocyclic rings mentioned in the meanings for R additionally to carry as substituents up to three $C_1$-$C_4$-alkyl groups, hydroxyl groups, carboxyl groups, sulfo groups or $C_1$-$C_4$-alkoxycarbonyl groups, or a radical of the formula

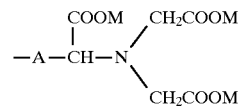

where A is a $C_1$-$C_{12}$-alkylene bridge or a chemical bond, and M is hydrogen, alkali metal, alkaline earth metal, ammonium or substituted ammonium in the appropriate stoichiometric amounts, by reacting corresponding 2-substituted glycines or 2-substituted glycinonitriles or doubled glycines of the formula

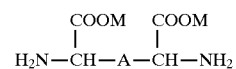

or doubled glycinonitriles of the formula

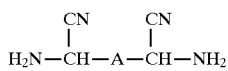

or precursors of the glycine derivatives named as starting material with formaldehyde and alkali metal cyanide in aqueous medium at a pH of from 8 to 14, wherein from 0.5 to 30% of the amount of alkali metal cyanide required for the reaction are added to the glycine derivatives or precursors thereof, and subsequently the remaining amount of alkali metal cyanide and the formaldehyde are simultaneously metered in over a period of from 0.5 to 12 hours.

In the prior art embodiments of the "alkaline" Strecker reaction of amino acids, usually either the total amounts of formaldehyde and alkali metal cyanide are added all at once before the reaction starts, or the total amount of alkali metal cyanide is added and then the formaldehyde is metered in.

The process according to the invention differs therefrom in that the glycine derivatives or their precursors used as starting material are introduced into the aqueous reaction medium and heated to the reaction temperature, after which from 0.5 to 30%, preferably 1.0 to 15%, in particular 2.0 to 10%, of the amount of alkali metal cyanide required for the reaction are added all at once. Subsequently, the remaining amount of alkali metal cyanide and the formaldehyde are metered in simultaneously over a period of from 0.5 to 12, preferably 1 to 8, in particular 2 to 6, hours. It is moreover possible for the additions of alkali metal cyanide and formaldehyde to be completed at the same time or different times, and in the latter case the formaldehyde addition is usually completed later. Following the addition of the reactants, the reaction is normally allowed to continue for from 1 to 10, preferably 2 to 5, hours under the reaction conditions.

Alkali metal cyanide, usually sodium or potassium cyanide, and formaldehyde are normally used as aqueous solutions. It is also possible, however, to add these components for example in solid form (in the case of formaldehyde for example as paraformaldehyde). The reaction medium usually employed is water, which in most cases dissolves the final products and the reaction components used to a sufficient extent. However, it is also possible to use mixtures of water and water-miscible organic solvents such as alcohols, eg. methanol, ethanol or isopropanol, when the intention is, for example, to prepare glycine-N,N-diacetic acids I with a more hydrophobic, ie. longer-chain or more voluminous, radical R.

In a preferred embodiment of the process according to the invention, the pressure in the reaction apparatus is from 100 to 1000 mbar, preferably 300 to 900 mbar, in particular 500 to 800 mbar, before and/or during the reaction.

In another preferred embodiment of the process according to the invention, an inert gas such as air, nitrogen or argon is passed through the reaction mixture or the reactants initially present (stripping with inert gas) before and/or during the reaction.

It is also possible to combine the two preferred embodiments mentioned. The pressure reduction and the passing through of inert gas serve, in particular, to improve the removal of ammonia which is still present in the precursors or is formed during the reaction from the reaction system. It has also emerged that reaction under atmospheric pressure or use of a slightly elevated pressure leads to unwanted high NTA contents (usually >2% by weight) in the final product.

The reaction according to the invention of glycine derivatives or their precursors with formaldehyde and alkali metal cyanide is normally carried out at from 40° to 110° C., in particular 60° to 100° C., especially 75° to 90° C. The pH of the aqueous reaction medium is from 8 to 14, preferably 10 to 13.

It is expedient to use from 2.0 to 3.0 mol, in particular 2.0 to 2.6 mol, of formaldehyde, preferably in the form of its approximately 30% by weight aqueous solution, and a total of from 2.0 to 3.0 mol, in particular 2.0 to 2.6 mol, of alkali metal cyanide, preferably as approximately 20–40% by weight aqueous solution, per mol of glycine derivative or its precursor used as starting material. Normally used as starting material are aqueous solutions of the appropriate glycine derivatives or precursors with a glycine derivative or precursor content of from 10 to 50% by weight, in particular 25 to 45% by weight.

The process according to the invention surprisingly also gives excellent results when raw material which derives from the industrial synthesis of glycine derivatives or their precursors and has not been purified, ie. as a rule not isolated as solid or, for example, crystallized to remove additional constituents, or mother liquors produced in such syntheses, is used as starting material. Precursors of glycine derivatives mean, for example in the case of alanine (R=CH$_3$), alanine amino nitrile or 5-methylhydantoin, the latter being produced, for example, by reaction of acetaldehyde, alkali metal cyanide and ammonium carbonate. The usual industrial synthesis of alanine is carried out by Strecker reaction of acetaldehyde, hydrocyanic acid and ammonia. Enzymatically prepared alanine can also be used without isolation of solid.

The process according to the invention can be used with particularly good results for preparing glycine-N,N-diacetic acid derivatives I where R is $C_1$-$C_{20}$-alkyl, $C_2$-$C_{20}$-alkenyl or a radical of the formula

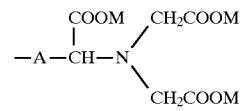

The process according to the invention is very particularly suitable for preparing α-alanine-N,N-diacetic acid (R=CH$_3$) and its alkali metal, ammonium and substituted ammonium salts.

Particularly suitable salts of this type are the sodium, potassium and ammonium salts, especially the trisodium, tripotassium and triammonium salt, and organic triamine salts with a tertiary nitrogen atom.

Particularly suitable bases on which the organic amine salts are based are tertiary amines such as trialkylamines with from 1 to 4 carbon atoms in the alkyl, eg. trimethylamine and triethylamine, and trialkanolamines with 2 or 3 carbon atoms in the alkanol residue, preferably triethanolamine, tri-n-propanolamine or triisopropanolamine.

Calcium and magnesium salts are used in particular as alkaline earth metal salts.

Besides methyl, suitable straight-chain or branched alk(en)yl radicals for R are, in particular, $C_2$-$C_{17}$-alkyl and -alkenyl, of these in particular straight-chain radicals derived from saturated or unsaturated fatty acids. Examples of individual R radicals are: ethyl, n-propyl, isopropyl, n-butyl, isobutyl, sec-butyl, tert-butyl, n-pentyl, isopentyl, sec-pentyl, tert-pentyl, neopentyl, n-hexyl, n-heptyl, 3-heptyl (derived from 2-ethylhexanoic acid), n-octyl, isooctyl (derived from isononanoic acid), n-nonyl, n-decyl, n-undecyl, n-dodecyl, isododecyl (derived from isotridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). Mixtures may also occur for R, especially those derived from naturally occurring fatty acids and from synthetic industrial acids, for example from the oxo synthesis.

Examples of the $C_1$-$C_4$-, $C_1$-$C_{12}$- and $C_1$-$C_{20}$-alkyl groups which are also mentioned are also to be regarded as the corresponding radicals detailed above for R.

Used as $C_1$-$C_2$-alkylene bridges A are, in particular, polymethylene groups of the formula -$(CH_2)k$- where k is from 2 to 12, in particular from 2 to 8, ie. 1,2-ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred. However, branched $C_1C_{12}$-alkylene groups may also occur, eg. -$CH_2CH(CH_3)CH_2$-, -$CH_2C(CH_3)_2CH_2$-, -$CH_2CH(C_2H_5)$- or -$CH_2CH(CH_3)$-.

The $C_1$-$C_{30}$-alkyl and $C_2$-$C_{30}$-alkenyl groups may carry up to 5, in particular up to 3, additional substituents of the said type and be interrupted by up to 5, in particular up to 3, nonadjacent oxygen atoms. Examples of such substituted alk(en)yl groups are -$CH_2OH$, -$CH_2CH_2OH$, -$CH_2CH_2$-O-$CH_3$, -$CH_2CH_2$-O-$CH_2CH_2$-O-$CH_3$, -$CH_2$-O-$CH_2CH_3$, -$CH_2$-O-$CH_2CH_2$-OH, -$CH_2$-CHO, -$CH_2$-OPh, -$CH_2$-COOCH_3 or $CH_2CH_2$-COOCH_3.

Particularly suitable alkoxylate groups are those where m and n are each from 0 to 30, in particular 0 to 15. $A^1$ and $A^2$ are groups derived from butylene oxide and, in particular, from propylene oxide and from ethylene oxide. Pure ethoxylates and pure propoxylates are of particular interest, but ethylene oxide/propylene oxide block structures may also occur.

Suitable five- or six-membered unsaturated or saturated heterocyclic rings which have up to three hetero atoms from the group consisting of nitrogen, oxygen and sulfur and which can additionally be benzo-fused and substituted by the identified radicals:

tetrahydrofuran, furan, tetrahydrothiophene, thiophene, 2,5-dimethylthiophene, pyrrolidine, pyrroline, pyrrole, isoxazole, oxazole, thiazole, pyrazole, imidazoline, imidazole, 1,2,3-triazolidine, 1,2,3- and 1,2,4-triazole, 1,2, 3-, 1,2,4- and 1,2,5-oxadiazole, tetrahydropyran, dihydropyran, 2H- and 4H-pyran, piperidine, 1,3- and 1,4-dioxane, morpholine, pyrazane, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, isoindoline, benzoxazole, indazole, benzimidazole, chroman, isochroman, 2H- and 4H-chromene, quinoline, isoquinoline, 1,2,3,4-tetrahydroisoquinoline, cinnoline, quinazoline, quinoxaline, phthalazine and benzo-1,2,3-triazine.

N-H groups in said heterocyclic rings ought where possible to be present in derivatized form, for example as N-alkyl groups.

Substituted phenyl nuclei or heterocyclic rings preferably have two (identical or different) or, in particular, a single substituent.

Examples of unsubstituted or substituted phenylalkyl groups and alkyl groups carrying heterocyclic rings for R are benzyl, 2-phenylethyl, 3-phenylpropyl, 4-phenylbutyl, o-, m- or p-hydroxybenzyl, o-, m- or p-carboxybenzyl, o-, m- or p-sulfobenzyl, o-, m- or p-methoxy- or -ethoxycarbonylbenzyl, 2-furylmethyl, N-methyl-4-piperidinylmethyl or 2-, 3- or 4-pyridinylmethyl.

Preferred substituents on phenyl nuclei and on heterocyclic rings are groups which confer solubility in water, such as hydroxyl groups, carboxyl groups or sulfo groups.

The compounds I prepared by the process according to the invention may be in the form of racemates or of enantiomerically pure compounds in respect of the α-carbon atom, depending on whether D,L-glycine derivatives or the corresponding D or L forms are used as starting material.

The free acids of compounds I can be obtained by acidification by conventional methods.

The specific way of carrying out the reaction in the process according to the invention very substantially suppresses the formation of unwanted NTA in the product, and the amounts of NTA are distinctly less than 2% by weight, usually 0.1–0.3% by weight. The yields are distinctly higher than in prior art processes: the yield in the preparation of MGDA trisodium salt is >95% based on alanine, compared with about 90% by the process disclosed in (4). In the process according to the invention, the side reaction of the formation of formate from cyanide is substantially suppressed and, compared- with the process disclosed in (4), the average holdup time of cyanide in the alkaline solution is reduced in the process according to the invention. Surprisingly, the formation of iminodiacetic acid as byproduct is not observed, in contrast to the hydrolysis, described in (1), of the corresponding trinitrile to MGDA trisodium salt.

A particular advantage of the process according to the invention is the possibility of using in place of pure glycine derivatives also corresponding crude mixtures as produced, for example, in the Strecker amino acid synthesis, for example of alanine, or else enzymatically, but also corresponding precursors such as hydantoins. This procedure is particularly economic because the costly product removal at the isoelectric point which is normally necessary following the amino acid preparation is unnecessary in this case. It is thus possible to save on reagents for adjusting the pH and to avoid separation losses because the amino acid normally remaining in the mother liquor of the amino acid synthesis is also used. It is possible and beneficial for the alkali metal salt from the amino acid synthesis to be reacted directly, without further addition of alkali, and without loss of yield and selectivity. Hydantoins can just like nitriles be hydrolyzed in a mixture by adding the appropriate amount of alkali and be directly reacted in one step with formaldehyde in aqueous alkali metal cyanide in the manner according to the invention, and this method overall provides a higher total yield with, at the same time, a simpler process compared with reaction of amino acid isolated by precipitation.

EXAMPLES

EXAMPLE 1

Preparation of MGDA trisodium salt from alanine 42.0 kg of 50% by weight aqueous sodium hydroxide solution were dissolved in 84 kg of water. 44.5 kg of D,L-α-alanine were introduced into this solution at room temperature over the course of 30 min. The mixture was then heated to 80° C. and the pressure was reduced to 500 mbar. Over the course of 3 h, 186 kg of 33% by weight aqueous NaCN solution and, starting 15 min later, likewise over the course of 3 h, 125 kg of 30% by weight aqueous formaldehyde solution were introduced. The temperature was kept at 80° C. throughout this time, and the ammonia which was formed was stripped out. After a further 3 h at 80° C., the residue comprised 335 kg of a pale yellow solution with an iron-binding capacity of 1.47 mmol/g, corresponding to a 98.5% yield of MGDA trisodium salt. The NTA content found by HPLC was 0.24% by weight.

EXAMPLE 2

Preparation of MGDA trisodium salt from crude alanine mixture 27 g of hydrocyanic acid were added dropwise to 204 g of 25% by weight aqueous ammonia at 0° C. Then, over the course of 20 min, 44 g of acetaldehyde were added dropwise to the resulting solution at 10° C. and, after a further 2 h at 20° C., the HCN conversion was 98%. 204 g of 21% by weight aqueous NaOH were added at this temperature, and the mixture was stirred for 5 h. It was then heated at 60° C. for 1 h and at 95° C. for 3 h, stripping with nitrogen until no more ammonia was produced.

Then, at 80° C., 7.5 g of 33% by weight sodium cyanide solution were added to this crude alanine solution, and subsequently 200 g of 30% by weight aqueous formaldehyde solution and 290 g of 33% by weight sodium cyanide solution were metered in simultaneously by an automatic metering device over the course of 3 h under 800 mbar while passing nitrogen in. After the addition was complete, the mixture was stirred under the stated conditions for 2 h, to result in 812 g of a pale yellow solution with an iron-binding capacity of 0.95 mmol/g, corresponding to 77% of theory based on acetaldehyde. The NTA content was 0.27% by weight.

EXAMPLE 3

Preparation of MGDA from 5-methylhydantoin 106 g of ammonium cabonate dissolved in 500 ml of water were mixed with 149 g of 33% by weight aqueous sodium cyanide solution at 10° C. and then, over the course of 2 h, 44 g of acetaldehyde were added dropwise and, after the addition was complete, the mixture was stirred at 20° C. for 24 h, after which the cyanide conversion was 100%. 3.40 g of imidazole were added to the mixture and, at 95° C., a total of 120 g of NaOH was introduced in portions. After 64 h at about 100° C. while stripping with nitrogen, 8 g of 33% by weight aqueous sodium cyanide solution were added to this 5-methylhydantoin-containing solution. At 80° C. under 800 mbar and while stripping with nitrogen, 280 g of 33% by weight aqueous sodium cyanide solution and 200 g of 30% by weight aqueous formaldehyde were added simultaneously over the course of 3 h. After a further 3 h under these conditions, 631 g of a solution with an iron-binding capacity of 1.28 mmol/g, corresponding to 81% of theory, were obtained with an NTA content of 0.25% by weight.

We claim:

1. A process for preparing glycine-N,N-diacetic acid derivatives of the general formula I

 (I)

where R is $C_1$-$C_{30}$-alkyl or $C_2$-$C_{30}$-alkenyl, each of which can additionally carry as substituents up to 5 hydroxyl groups, formyl groups, $C_1$-$C_4$-alkoxy groups, phenoxy groups or $C_1$-$C_4$-alkoxycarbonyl groups and can be interrupted by up to 5 nonadjacent oxygen atoms, or alkoxylate groups of the formula -$(CH_2)_k$-O-$(A^1O)_m$-$(A^2O)_n$-Y, where $A^1$ and $A^2$ are, independently of one another, 1,2-alkylene groups having 2 to 4 carbon atoms, Y is hydrogen, $C_1$-$C_{12}$-alkyl, phenyl or $C_1$-$C_4$-alkoxycarbonyl, and k is 1, 2 or 3 and m and n are each from 0 to 50, ii- being necessary for the total of m+n to be at least 4, phenylalkyl groups having 1 to 20 carbon atoms in the alkyl, phenyl, a five- or six-membered unsaturated or saturated heterocyclic ring which has up to three hetero atoms from the group consisting of nitrogen, oxygen and sulfur and which can additionally be benzo-fused, it also being possible for all the phenyl nuclei and heterocyclic rings mentioned in the meanings for R additionally to carry as substituents up to three $C_1$-$C_4$-alkyl groups, hydroxyl groups, carboxyl groups, sulfo groups or $C_1$-$C_4$-alkoxycarbonyl groups, or a radical of the formula

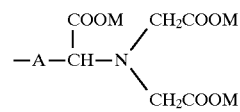

where A is a $C_1$-$C_{12}$-alkylene bridge or a chemical bond, and M is hydrogen, alkali metal, alkaline earth metal, ammonium or substituted ammonium in the appropriate stoichiometric amounts, by reacting corresponding 2-substituted glycines or 2-substituted glycinonitriles or doubled glycines of the formula

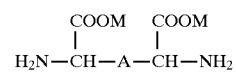

or doubled glycinonitriles of the formula

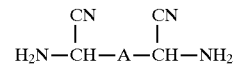

or precursors of the glycine derivatives named as starting material with formaldehyde and alkali metal cyanide in aqueous medium at a pH of from 8 to 14, and at a pressure of from 300 from 900 mbar wherein from 0.5 to 30% of the amount of alkali metal cyanide required for the reaction are added to the glycine derivatives or precursors thereof, and subsequently the remaining amount of alkali metal cyanide and the formaldehyde are simultaneously metered in over a period of from 0.5 to 12 hours.

2. A process for preparing glycine-N,N-diacetic acid derivatives I as claimed in claim 1, wherein the pressure in the reaction apparatus is from 500 to 800 mbar before and/or during the reaction.

3. A process for preparing glycine-N,N-diacetic acid derivatives I as claimed in claim 1, wherein an inert gas is passed through the reaction mixture or the reactants initially present before and/or during the reaction.

4. A process for preparing glycine-N,N-diacetic acid derivatives I as claimed in claim 1, wherein unpurified raw material derived from the industrial synthesis of glycine derivatives or their precursors, or mother liquors produced in such syntheses, is used as starting material.

5. A process for preparing glycine-N,N-diacetic acid derivatives I as claimed in claim 1, where R is $C_1$-$C_{20}$-alkyl, $C_2$-$C_{20}$-alkenyl or a radical of the formula

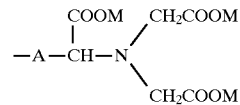

6. A process for preparing α-alanine-N,N-diacetic acid and its alkali metal, ammonium and substituted ammonium salts as claimed in claim 1.

* * * * *